(12) United States Patent
Xiao et al.

(10) Patent No.: US 12,392,915 B2
(45) Date of Patent: Aug. 19, 2025

(54) CALIBRATION DEVICE FOR RADON EXHALATION RATE MEASURING INSTRUMENT AND RADON EXHALATION RATE CONTROL METHOD

(71) Applicant: University of South China, Hengyang (CN)

(72) Inventors: Detao Xiao, Hengyang (CN); Weigang Li, Hengyang (CN); Shoukang Qiu, Hengyang (CN)

(73) Assignee: University of South China, Hengyang (CN)

( * ) Notice: Subject to any disclaimer, the term of this patent is extended or adjusted under 35 U.S.C. 154(b) by 249 days.

(21) Appl. No.: 18/351,071

(22) Filed: Jul. 12, 2023

(65) Prior Publication Data
US 2024/0219593 A1 Jul. 4, 2024

(30) Foreign Application Priority Data
Dec. 29, 2022 (CN) .......................... 202211702731.1

(51) Int. Cl.
*G01T 7/00* (2006.01)
*G01N 33/00* (2006.01)
*G01T 1/167* (2006.01)
*G01T 1/178* (2006.01)

(52) U.S. Cl.
CPC ......... *G01T 7/005* (2013.01); *G01N 33/0055* (2013.01); *G01T 1/167* (2013.01); *G01T 1/178* (2013.01)

(58) Field of Classification Search
CPC ......... G01T 7/005; G01T 1/167; G01T 1/178; G01N 33/0055
See application file for complete search history.

(56) References Cited

FOREIGN PATENT DOCUMENTS

| CN | 108646286 A | * | 10/2018 | ............. G01T 7/005 |
|---|---|---|---|---|
| CN | 112946718 A | * | 6/2021 | ............. G01T 1/167 |

* cited by examiner

*Primary Examiner* — David P Porta
*Assistant Examiner* — Casey Bryant
(74) *Attorney, Agent, or Firm* — PROI Intellectual Property US (57) ABSTRACT

A calibration device for a radon exhalation rate measuring instrument and radon exhalation rate control method thereof is provided, and relates to the field of radon exhalation rate measurement. The device includes a diffusive solid radon source, a solid radon source containing chamber, a radon accumulation chamber, a diffusion medium, an air pressure balancing device, a support frame and a fixture; a circular cone opening at a bottom of the radon accumulation chamber is connected with the solid radon source containing chamber, a top of the radon accumulation chamber is sealed by the diffusion medium, the diffusion medium includes a plasterboard and a high-density wood board, the high-density wood board is on the plasterboard, the air pressure balancing device is connected with the radon accumulation chamber, and configured to maintain dynamic balance between the radon accumulation chamber and ambient atmospheric pressure.

16 Claims, 5 Drawing Sheets

CALIBRATION DEVICE FOR RADON EXHALATION RATE MEASURING INSTRUMENT AND RADON EXHALATION RATE CONTROL METHOD

CROSS-REFERENCE TO RELATED APPLICATION

This patent application claims the benefit and priority of Chinese Patent Application No. 202211702731.1 filed with the China National Intellectual Property Administration on Dec. 29, 2022, the disclosure of which is incorporated by reference herein in its entirety as part of the present application.

TECHNICAL FIELD

The present disclosure relates to the field of radon exhalation rate measurement, and in particular, to a calibration device for a radon exhalation rate measuring instrument and a radon exhalation rate control method.

BACKGROUND

Ubiquitous Radon is the second leading cause of lung cancer after smoking, and is ranked as one of the 19 most carcinogenic substances by the World Health Organization. The harm of radon to human health and the monitoring and prevention and controlling of radon (especially indoor radon) have been paid more and more attention by the public. The radon in the environment mainly comes from the exhalation of the medium surface. For the safety of environment, ecology and human settlements, monitoring and controlling of radon sources put forward technical requirements for the measurement reliability of radon exhalation rate on the medium surface. It is desired to establish an experimental and calibration device for radon exhalation rate measuring instrument, that is, a standard device for radon exhalation rate.

In the prior art, Patent Application No. 201810557524.9 provides a reference device and method for stably controlling the radon exhalation rate, which includes a horizontal table, gas flow solid radon source, an air pump, an adjustment chamber and so on for adjusting the radon exhalation rate. The radon exhalation rate is controlled mainly by changing the chamber volume of the adjustment chamber, without purchasing a large number of standard radon sources with different source strengths, thereby reducing purchase cost and later maintenance cost of the device. However, the present disclosure has disadvantages of being unable to eliminate the influence of ambient air pressure inside and outside the device, and poor uniformity and stability.

SUMMARY

An objective of embodiments of the present disclosure is to provide a calibration device for a radon exhalation rate measuring instrument and radon exhalation rate control method, which improves the stability and uniformity of a radon exhalation rate of a surface of a medium of the calibration device for the radon exhalation rate measuring instrument, so as to improve the accuracy of verifying the radon exhalation rate measuring instrument.

To achieve the above objective, the present disclosure provides the following solution.

A calibration device for a radon exhalation rate measuring instrument, including a diffusive solid radon source, a solid radon source containing chamber, a radon accumulation chamber, a diffusion medium and an air pressure balancing device, where
the radon accumulation chamber is shaped as an inverted cone, a circular cone opening at a bottom of the radon accumulation chamber is connected with the solid radon source containing chamber, a top of the radon accumulation chamber is connected with the diffusion medium, the diffusion medium includes a plasterboard and a high-density wood board, the plasterboard is located above the radon accumulation chamber, the high-density wood board is overlapped on the plasterboard, the air pressure balancing device is connected with the radon accumulation chamber, and configured to maintain air pressure dynamic balance between the radon accumulation chamber and ambient atmosphere;
a radon exhalation rate of a surface of the diffusion medium is determined according to a diffusion coefficient of radon in the diffusion medium, a thickness of a diffusion medium layer, and an activity of a solid radon source in the solid radon source containing chamber;
the radon exhalation rate is adjusted by changing the activity of the solid radon source in the solid radon source containing chamber and the thickness of the diffusion medium layer.

Optionally, the calibration device further includes a support frame and a fixture for fixing the diffusion medium layer, where the fixture includes an upper fastening flange, a lower fastening flange, a fastening screw and a holding plate, the holding plate is arranged at an edge of the diffusion medium layer for holding, the fastening screw is configured to have an adjustable length and pass through the holding plate, and the upper fastening flange and the lower fastening flange are respectively located at two ends of the fastening screw for fastening the holding plate;
the support frame is connected with a bottom of the fixture, the support frame is configured to support the radon accumulation chamber, and both the support frame and the radon accumulation chamber are made of stainless steel material;
a universal wheel is arranged at a bottom of the support frame.

Optionally, the calibration device further includes a housing, where the housing is cylindrical, the housing is sleeved on outer sides of the support frame and the diffusion medium, and the housing is made of stainless steel material.

Optionally, the radon accumulation chamber is connected with the solid radon source containing chamber in a flange connection manner, and has a silicone gasket provided therebetween.

Optionally, a silicone gasket is arranged between the high-density wood board and the plasterboard.

Optionally, the air pressure balancing device includes a U-shaped connecting pipe and an air pressure balancing bottle, the air pressure balancing bottle is connected with the radon accumulation chamber through the U-shaped connecting pipe, and liquid in the air pressure balancing bottle is a saline mixture with a salt concentration exceeding a predetermined salt concentration.

Optionally, a side wall of the radon accumulation chamber is provided with a first inlet and a second inlet, which are symmetrically distributed on the side wall of the radon accumulation chamber, and through which a predetermined amount of radon is rapidly inflated from a gas flow solid radon source into the radon accumulation chamber.

Optionally, a cross support is arranged at a top opening of the radon accumulation chamber.

The present disclosure further discloses a radon exhalation rate control method, which is applied to the calibration device, and includes:

adjusting the radon exhalation rate of the calibration device by changing the activity of the solid radon source in the radon accumulation chamber and the thickness of the diffusion medium layer of the calibration device, and calibrating different verified radon exhalation rate measuring instruments by adjusting the radon exhalation rate of the calibration device;

an adjustment process for a radon exhalation rate to be adjusted includes:

step 1: determining thicknesses of the plasterboard and the high-density wood board in the diffusion medium;

step 2: determining a relationship among diffusive solid radon sources with different activities and radon exhalation rates and radon concentrations in the radon accumulation chamber;

step 3: based on the relationship among the diffusive solid radon sources with different activities and the radon exhalation rates and the radon concentrations in the radon accumulation chamber, selecting a diffusive solid radon source according to the radon exhalation rate to be adjusted;

step 4: determining a stable radon concentration in the radon accumulation chamber according to the selected diffusive solid radon source;

step 5: placing the selected diffusive solid radon source in the solid radon source containing chamber, inflating the radon accumulation chamber with a predetermined amount of radon from a gas flow solid radon source, and waiting for the radon concentration in the radon accumulation chamber to reach a balance state;

when the radon exhalation rate to be adjusted changes, if the thicknesses of the plasterboard and the high-density wood board in the diffusion medium do not change, repeating steps 3-5 to adjust the radon exhalation rate;

when the radon exhalation rate to be adjusted changes, if the thicknesses of the plasterboard and the high-density wood board in the diffusion medium change, repeating steps 1-5 to adjust the radon exhalation rate.

According to specific embodiments provided by the present disclosure, the following technical effects are disclosed.

The present disclosure adopts the plasterboard and the high-density wood board with adjustable thicknesses as the diffusion medium, makes use of the uniformity of radon diffusion in the high-density wood board and the radon resistance of the plasterboard, and adopts the pressure balancing device to eliminate the influence of the atmospheric pressure change on the radon exhalation rate of the device, so as to realize the uniformity and stability of the radon exhalation rate on the surface of the device. By inflating the radon accumulation chamber with radon chamber matching the solid radon source, the device can quickly reach steady state and produce stable and uniform expected radon exhalation rate, which improves the efficiency of radon exhalation rate adjustment.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

DESCRIPTION OF REFERENCE SIGNS a, solid radon source containing chamber; b, radon accumulation chamber; c, plasterboard; d, high-density wood board; e, fastening flange; f, fastening screw; g, positioning flange; h, housing; i, support frame; j, universal wheel; k, air pressure balancing device; l, air hole; m, fixture.

DETAILED DESCRIPTION OF THE EMBODIMENTS

The technical solutions in the embodiments of the present disclosure will be described below clearly and completely with reference to the accompanying drawings in the embodiments of the present disclosure. Apparently, the described embodiments are merely some rather than all of the embodiments of the present disclosure. All other embodiments obtained by those of ordinary skill in the art based on the embodiments of the present disclosure without creative efforts shall fall within the protection scope of the present disclosure.

An objective of some embodiments of the present disclosure is to provide a calibration device for a radon exhalation rate measuring instrument and a radon exhalation rate control method, which improve stability and uniformity of the calibration device for the radon exhalation rate measuring instrument, so as improve calibration accuracy of the radon exhalation rate measuring instrument.

To make the above objective, features, and advantages of the present disclosure more fully apparent, the present disclosure will be further described in detail below in conjunction with the accompanying drawings and specific embodiments.

Embodiment 1

Figure 1:
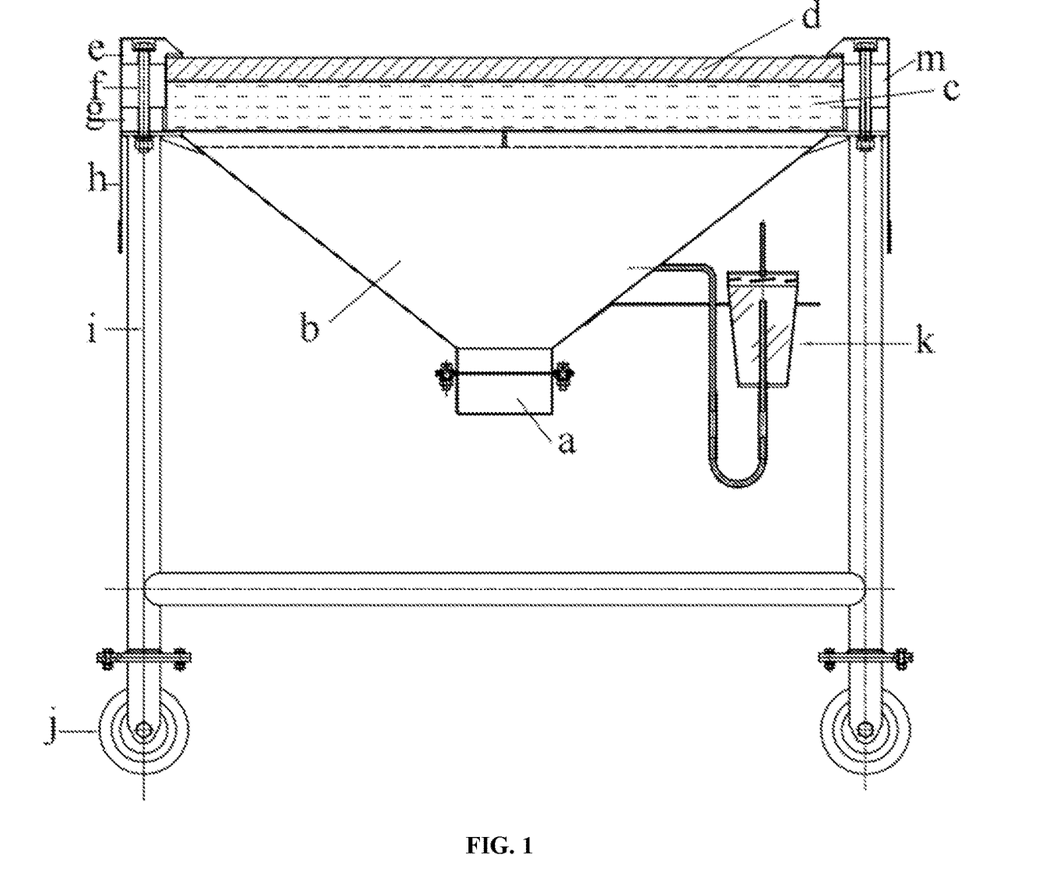
FIG. 1 is a schematic structural diagram of a calibration device for a radon exhalation rate measuring instrument according to the present disclosure.

FIG. 1 is a schematic structural diagram of a calibration device for a radon exhalation rate measuring instrument according to the present disclosure. As shown in FIG. 1, a calibration device for a radon exhalation rate measuring instrument includes a diffusive solid radon source, a solid radon source containing chamber, a radon accumulation chamber, a diffusion medium and an air pressure balancing device.

The diffusive solid radon source is simply referred to as a solid radon source.

The radon accumulation chamber is shaped as an inverted cone, a circular cone opening at a bottom of the radon accumulation chamber is connected with the solid radon source containing chamber, a top of the radon accumulation chamber is connected with the diffusion medium, the diffusion medium includes a plasterboard and a high-density wood board, the plasterboard is located above the radon accumulation chamber, the high density wood board is overlapped on the plasterboard, the air pressure balancing device is connected with the radon accumulation chamber, and the air pressure balancing device is used to maintain air pressure dynamic balance between the radon accumulation chamber and the ambient atmosphere.

Figure 5:
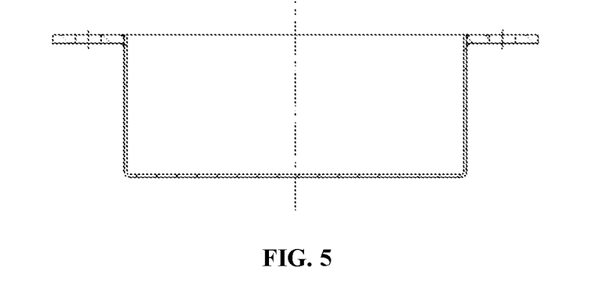
FIG. 5 is a side view of a solid radon source containing chamber according to the present disclosure.
Figure 6:
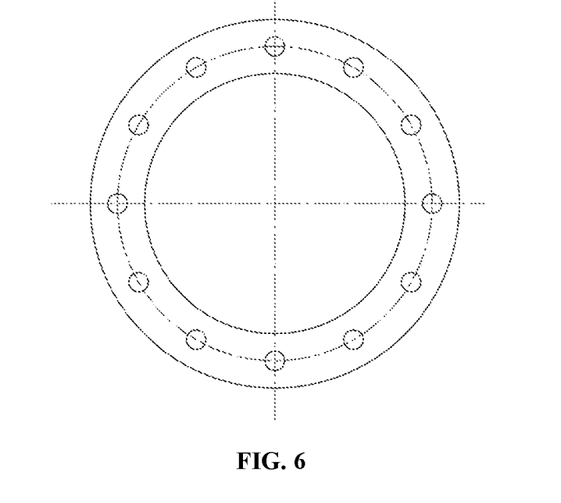
FIG. 6 is a top view of the solid radon source containing chamber according to the present disclosure.

The solid radon source containing chamber is shown in FIGS. 5 and 6.

A radon exhalation rate of a surface of the diffusion medium is determined according to a diffusion coefficient of radon in the diffusion medium, a thickness of a diffusion medium layer, and an activity of the solid radon source contained in a radon accumulation chamber.

The radon exhalation rate is adjusted by changing the activity of the solid radon source in the solid radon source containing chamber and the thickness of the diffusion medium layer.

The calibration device for the radon exhalation rate measuring instrument further includes a support frame and a fixture.

Figure 3:
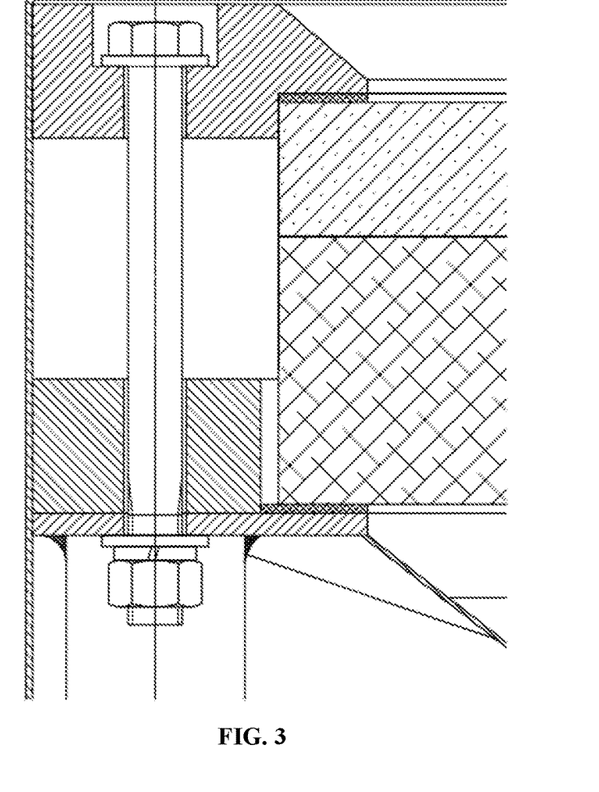
FIG. 3 is a schematic diagram showing connection of the diffusion medium according to the present disclosure.

The fixture is configured to fix the diffusion medium layer. As shown in FIG. 3, the fixture includes an upper fastening flange, a lower fastening flange, fastening screws and a holding plate. The holding plate is arranged at an edge of the diffusion medium layer for holding it, and each fastening screw is configured to have adjustable length and passes through the holding plate. The upper fastening flange and the lower fastening flange are respectively located at two ends of the fastening screw for fastening the holding plate.

The support frame is connected with a bottom of the fixture, the support frame is configured to support the radon accumulation chamber, and both the support frame and the radon accumulation chamber are made of stainless steel material.

Universal wheels are arranged at a bottom of the support frame.

The calibration device for the radon exhalation rate measuring instrument further includes a cylindrical housing, which is sleeved at outer sides of the support frame and the diffusion medium and is made of stainless steel material.

In addition to the stainless steel, the support frame, the radon accumulation chamber, and the housing can be made of other radon-impermeable metals.

Figure 2:
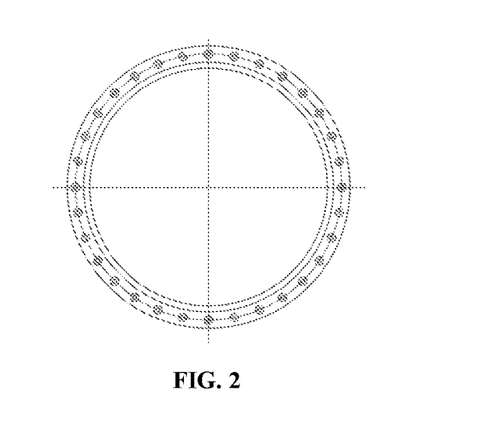
FIG. 2 is a schematic diagram of upper and lower fastening flanges for a diffusion medium according to the present disclosure.

The radon accumulation chamber is detachably connected with the solid radon source containing chamber, in a manner of a flange connection. As shown in FIGS. 2 and 3, the radon accumulation chamber and the solid radon source containing chamber have a silicone gasket provided therebetween, and are connected together by 1~N fastening screws in a flanged connection manner.

Figure 8:
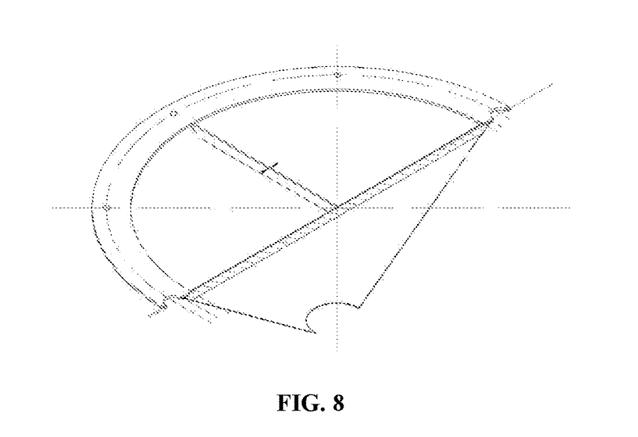
FIG. 8 is a schematic diagram of the radon accumulation chamber according to the present disclosure.

The radon accumulation chamber is integrally formed by stamping the radon-impermeable metal material, as shown in FIG. 8.

A silicone gasket is provided between the high-density wood board and the plasterboard.

Figure 4:
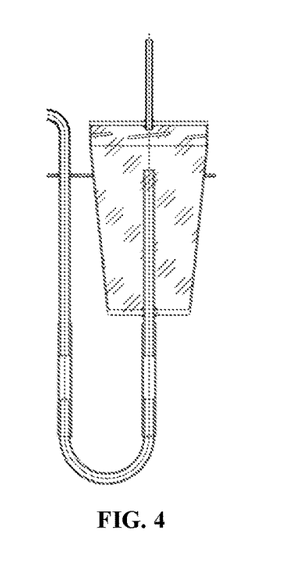
FIG. 4 is a schematic diagram of an air pressure balancing device according to the present disclosure.

As shown in FIG. 4, the air pressure balancing device includes a U-shaped connecting pipe and an air pressure balancing bottle connected with the radon accumulation chamber through the U-shaped connecting pipe. A liquid in the air pressure balancing bottle may be a high-concentration saline mixture (a saline mixture with a salt concentration exceeding a predetermined salt concentration). Alternatively, the liquid in the air pressure balancing bottle may also be other liquids impermeable to radon.

Figure 7:
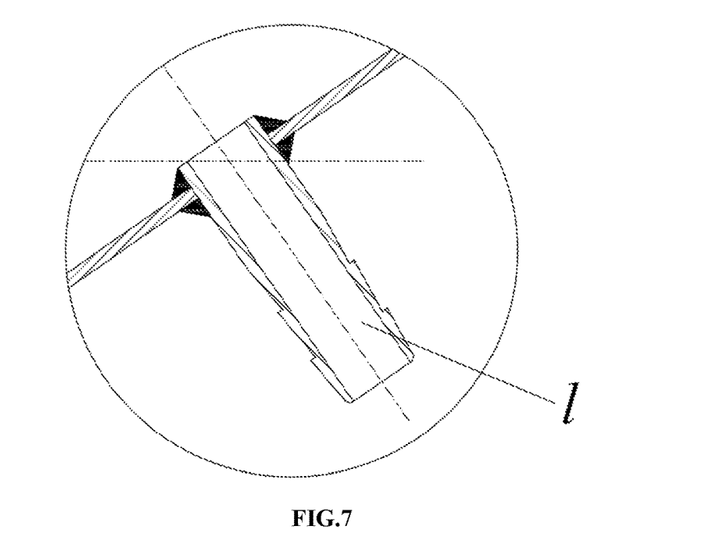
FIG. 7 is a schematic view of a peripheral air hole of a radon accumulation chamber according to the present disclosure.

A side wall of the radon accumulation chamber is provided with a first inlet and a second inlet, which are symmetrically distributed on the side wall of the radon accumulation chamber, and through which a predetermined amount of radon are inflated into the radon accumulation chamber from a gas flow solid radon source. Air holes/in the first inlet and the second inlet of the radon accumulation chamber are shown in FIG. 7.

The thicknesses of the high-density wood board and the plasterboard are adjustable.

As a specific implementation, the thickness of the high-density wood board is 30 mm, and the thickness of the plasterboard is 60 mm.

A cross support is arranged at a top opening of the radon accumulation chamber.

The air pressure balancing device of the present disclosure allows the dynamic balance between an air pressure in the radon accumulation chamber and the ambient atmospheric pressure, to minimize the influence of the seepage effect caused by the pressure gradient.

The diffusion medium is made of material with moderate radon transmittance, so that the migration rate of radon in the medium is slowed down and the radon exhalation rate on the medium surface is stable. The present disclosure adopts diffusion medium (a diffusion component) including a high-density wood board and a plasterboard.

In the present disclosure, the diffusion medium including a combination of a high-density wood board and a plasterboard overlapping one another, solves the problem that the high-density wood board has a poor resistance to radon and a good uniformity, and the plasterboard is relatively dense and has a certain resistance to radon and a poor uniformity. The integrated diffusion component formed by both of them can achieve excellent stable performance and uniform performance of the device.

In the present disclosure, one-dimensional upward diffusion of radon is realized by sealing each connecting part and the edge of the diffusion medium with high-performance sealant. in combined with the inverted cone design of the radon accumulation chamber. The calibration device for the radon exhalation rate measuring instrument is simple and portable, convenient to operate, and can be used for on-site measurement, which meets engineering requirement for rapidly measuring the radon exhalation rate.

In the present disclosure, a diffusive solid radon source with a high emanation coefficient and good stability is placed in the solid radon source containing chamber with a high emanation coefficient, the activity of the solid radon source can be adjusted in the range of $10^3$ Bq~$10^8$ Bq. and the emanation coefficient can reach (96±2)% under the conditions of ambient temperature 10° C.~45° C. and relative humidity 1~100%.

In the present disclosure, by arranging a first inlet and a second inlet on the side wall of the radon accumulation chamber, with a radon concentration in the radon accumulation chamber required upon reaching the balance through inflating the device by a gas flow radon source, the radon concentration in the radon accumulation chamber upon balance is quickly established, and the time for establishing the radon concentration upon balance by only the diffusion source is greatly shortened.

In the present disclosure, a calibration device for a radon exhalation rate measuring instrument is disclosed. The calibration device includes a diffusive solid radon source with a high emanation coefficient and good stability, a radon accumulation chamber, a diffusion medium, an air pressure balancing device, a support frame, a fixture, a housing and the like. By changing the activity of the radon source, the thickness of the radon diffusion medium and rapidly establishing the radon concentration in the radon accumulation chamber, the radon exhalation rate of device can be adjusted, and the adjustment range of the radon exhalation rate is enlarged. The radon exhalation rate of the device can be adjusted in the range of 5 mBq/(m²·s)~20000 mBq/(m²·s). The uniformity and stability of radon exhalation rate both are less than 5%, which are used for performance calibration and calibration of the radon exhalation rate measuring instrument.

Embodiment 2

In the present disclosure, 17000 Bq and 100000 Bq diffusive solid radon sources each are respectively placed in a solid radon source containing chamber of a calibration device for a radon exhalation rate measuring instrument. The radon accumulation chamber is shaped as an inverted cone, and is integrally formed by stamping the stainless steel material, so that the inner and outer surfaces are flat and smooth, without groove point. Further, the radon accumulation chamber is provided with two rapid inlets for inflating radon source and a connecting port for connecting with the air pressure balancing device, and provided, at the upper part thereof, with a cross support consisted of two mutually perpendicular strip-shaped components. Preferably, the diffusion medium adopts 30 mm high-density wood board and 60 mm plasterboard. The air pressure balancing device is connected with a U-shaped pipe, and contains saline with a concentration of about 90%, and the outlet of the air pressure balancing bottle is in a high humidity environment. The support frame and the housing are made of new stainless steel, the bottom of the support frame is equipped with universal wheels, and a surface of the housing is treated with baking paint. After test, the radon exhalation rates of the device surface (diffusion medium surface) are 21.57±1.02 mBq/(m²·s) and 197.28±2.32 mBq/(m²·s), respectively.

(1) Radon Exhalation Principle

Radon is released from the medium surface into the atmosphere, that is, radon exhalation from the medium surface. Radon is monatomic gas at a room temperature, which migrates due to the atomic thermal motion and convection. Radon atoms can move freely through connection gaps in the medium and are exhaled from the medium surface. The migration motion of radon in porous medium obeys Fick's First Law of Diffusion, that is, $$J = -D\nabla C$$

A second-order differential equation of diffusion and migration of the radon through the medium is shown in formula (2):

$$\frac{\partial C(x,t)}{\partial t} = D\frac{\partial^2 C(x,t)}{\partial x^2} - \lambda C(x,t), \tag{2}$$

Considering an inherent diffusion coefficient of the material itself, formula (3) is derived:

$$J = -D\frac{\partial C}{\partial x}, \tag{3}$$

where J is the radon exhalation rate of the surface of the device, with an unit of Bq/(m²·s); D is the diffusion coefficient of radon in the medium, with an unit of cm²/s; ∇C is the radon concentration gradient in the medium, and in a one-dimensional direction, $$\nabla C = \frac{\partial C}{\partial x};$$

x represents the coordinate with the inside normal of the medium surface as the axis; and t represents time. Because the diffusion coefficient of radon in the medium is determined by the medium material, the radon exhalation rate is affected by the radon concentration gradient in the medium.

(2) Measurement of the Diffusion Coefficient of Radon in the Medium

The diffusive solid radon source is placed in the radon accumulation chamber, the volume of the radon accumulation chamber is $V_1$, and the radon concentration in the radon accumulation chamber is denoted by $C_1$. A radon collection cover is provided for encompassing the medium surface so as to continuously verify the change of the radon concentration exhaled from the device. The volume of the radon collection cover is denoted by $V_2$, the radon concentration in the radon collection cover is denoted by $C_2$, the surface area of the exhalation medium is denoted by S, and the thickness of the medium is denoted by H. When the solubility coefficient of radon in the material is 1, $$\frac{C_2}{C_1} = \frac{SD}{\lambda H V_1}\left[1 + 2\sum_{n=1}^{\infty}(-1)^n \times \frac{1}{1 + \frac{n^2\pi^2 D}{\lambda H^2}}\right], \tag{4}$$

and when $D/H^2$ is large enough, formula (4) can be simplified to:

$$\frac{C_2}{C_1} = \frac{SD}{\lambda H V_1}, \tag{5}$$

$$D = \frac{\lambda H V_1 C_2}{S C_1}. \tag{6}$$

Formula (6) can be adapted to calculate radon diffusion coefficients of various media.

Table 1 below shows the calculated radon diffusion coefficients of the plasterboard and the high-density wood board.

TABLE 1

Radon diffusion coefficients of the plasterboard and the high-density wood board

| Material | Thickness/m | Decay constant of radon $\lambda$/s$^{-1}$ | Volume of radon accumulation chamber V/m$^3$ | Effective exhalation on area S/m$^2$ | Stable radon concentration of radon accumulation chamber $C_1$/(Bq/m$^3$) | Stable radon concentration of radon collection cover $C_2$/(Bq/m$^3$) | Diffusion coefficient D/(m$^2$/s) |
|---|---|---|---|---|---|---|---|
| Plasterboard | 0.06 | $2.1 \times 10^{-6}$ | 0.027 | 0.09 | 9813.64 | 763.03 | $2.94 \times 10^{-9}$ |
| High-density wood board | 0.03 | $2.1 \times 10^{-6}$ | 0.027 | 0.09 | 21473.39 | 16103.22 | $1.42 \times 10^{-8}$ |

(3) Diffusion of Radon in a Double-Layer Medium

Figure 9:
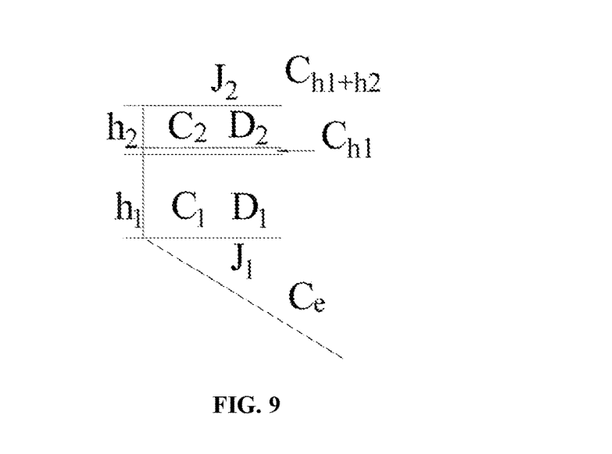
FIG. 9 is a schematic diagram showing parameters regarding diffusion of radon in a double-layer medium according to the present disclosure.

When there is no pressure gradient in the space environment, the migration of radon in the double-layer medium is pure diffusion migration. Based on the diffusion theory of radon, when the radon concentration reaches a stable balanced state in the space, a differential equation of radon diffusion in the double-layer medium is:

$$\begin{cases} D_1 \dfrac{d^2 C_1}{dx^2} - \lambda C_1 = 0 \\ D_2 \dfrac{d^2 C_2}{dx^2} - \lambda C_2 = 0 \end{cases} \quad (7)$$

The diffusion parameters of radon in the double-layer medium are shown in FIG. 9.

In formula (7), $C_1$: a radon concentration in the plasterboard, Bq/m$^3$;

$C_2$: a radon concentration in the high-density wood board, Bq/m$^3$;

$D_1$: a radon diffusion coefficient of the plasterboard, m$^2$/s;

$D_2$: a radon diffusion coefficient of the high-density wood board, m$^2$/s;

$\lambda$: a decay constant of radon, $2.1 \times 10^{-6}$ s$^{-1}$;

x: coordinates with the inside normal of the medium surface as the axis, m;

The formula (7) is solved to obtain:

$$\begin{cases} C_1 = A_1 \exp\left(\dfrac{\sqrt{\lambda D_1}}{D_1} x\right) - B_1 \exp\left(-\dfrac{\sqrt{\lambda D_1}}{D_1} x\right) \\ C_2 = A_2 \exp\left[\dfrac{\sqrt{\lambda D_2}}{D_2}(x - h_1)\right] - B_2 \exp\left[-\dfrac{\sqrt{\lambda D_2}}{D_2}(x - h_1)\right] \end{cases} \quad (8)$$

In Formula (8), $A_1$, $B_1$, $A_2$, and $B_2$ are intermediate parameters, $h_1$ indicates the thickness of the plasterboard, $h_2$ indicates the thickness of the high-density wood board:

$$A_1 = \frac{C_{h_1} - C_0 \exp\left(-\dfrac{h_1 \sqrt{\lambda D_1}}{D_1}\right)}{\exp\left(\dfrac{h_1 \sqrt{\lambda D_1}}{D_1}\right) - \exp\left(-\dfrac{h_1 \sqrt{\lambda D_1}}{D_1}\right)}, \quad (9)$$

$$B_1 = \frac{C_{h_1} - C_0 \exp\left(\dfrac{h_1 \sqrt{\lambda D_1}}{D_1}\right)}{\exp\left(\dfrac{h_1 \sqrt{\lambda D_1}}{D_1}\right) - \exp\left(-\dfrac{h_1 \sqrt{\lambda D_1}}{D_1}\right)}, \quad (10)$$

$$A_2 = \frac{C_{h_1+h_2} - C_{h_1} \exp\left(-\dfrac{h_2 \sqrt{\lambda D_2}}{D_2}\right)}{\exp\left(\dfrac{h_2 \sqrt{\lambda D_2}}{D_2}\right) - \exp\left(-\dfrac{h_2 \sqrt{\lambda D_2}}{D_2}\right)}, \quad (11)$$

$$B_2 = \frac{C_{h_1+h_2} - C_{h_1} \exp\left(\dfrac{h_2 \sqrt{\lambda D_2}}{D_2}\right)}{\exp\left(\dfrac{h_2 \sqrt{\lambda D_2}}{D_2}\right) - \exp\left(-\dfrac{h_2 \sqrt{\lambda D_2}}{D_2}\right)}, \quad (12)$$

where $C_{h_1}$ indicates the radon concentration of the medium surface when the medium thickness is $h_1$, $C_0$ indicates the radon concentration of the medium surface when the medium thickness approaches zero infinitely, and $C_0$ value is an ideal case and is not used for calculation, and $C_{h_1}+h_2$ indicates the radon concentration of the medium surface when the medium thickness is $h_1+h_2$.

When $x = 0$, $C_1 = A_1 - B_1 = C_0$;

when $x = h_1 + h_2$, $C_2 = C_{h_1+h_2}$;

when $x = h_1$, $C_{h_1} = A_2 - B_2$.

The radon exhalation rate of the lower surface of the preferred diffusion medium is:

$$J_1 = (A_1 + B_1)\sqrt{\lambda D_1}, \quad (13)$$

that is, $$J_1 = \frac{2 C_{h_1} \sqrt{\lambda D_1}}{\exp\left(\dfrac{h_1 \sqrt{\lambda D_1}}{D_1}\right) - \exp\left(-\dfrac{h_1 \sqrt{\lambda D_1}}{D_1}\right)}. \quad (14)$$

Similarly, the radon exhalation rate of the upper surface of the preferred diffusion medium is:

$$J_2 = \frac{2C_{h_1+h_2}\sqrt{\lambda D_2} - C_{h_1}\sqrt{\lambda D_2}\left[\exp\left(\frac{h_2\sqrt{\lambda D_2}}{D_2}\right) + \exp\left(-\frac{h_2\sqrt{\lambda D_2}}{D_2}\right)\right]}{\exp\left(\frac{h_2\sqrt{\lambda D_2}}{D_2}\right) - \exp\left(-\frac{h_2\sqrt{\lambda D_2}}{D_2}\right)}, \quad (15)$$

The ratio of the radon exhalation rate of the lower surface and the radon exhalation rate of the upper surface of the preferred diffusion module is:

$$\frac{J_1}{J_2} = \frac{\left[\exp\left(\frac{h_2\sqrt{\lambda D_2}}{D_2}\right) - \exp\left(-\frac{h_2\sqrt{\lambda D_2}}{D_2}\right)\right] 2C_{h_1}\sqrt{\lambda D_1}}{\left[\exp\left(\frac{h_1\sqrt{\lambda D_1}}{D_1}\right) - \exp\left(-\frac{h_1\sqrt{\lambda D_1}}{D_1}\right)\right]} \quad (16)$$

$$\left\{2C_{h_1+h_2}\sqrt{\lambda D_2} - C_{h_1}\sqrt{\lambda D_2}\left[\exp\left(\frac{h_2\sqrt{\lambda D_2}}{D_2}\right) + \exp\left(-\frac{h_2\sqrt{\lambda D_2}}{D_2}\right)\right]\right\}$$

that is, $J_1 = kJ_2$, (17)

where $k = \dfrac{\left[\exp\left(\frac{h_2\sqrt{\lambda D_2}}{D_2}\right) - \exp\left(-\frac{h_2\sqrt{\lambda D_2}}{D_2}\right)\right] 2C_{h_1}\sqrt{\lambda D_1}}{\left[\exp\left(\frac{h_1\sqrt{\lambda D_1}}{D_1}\right) - \exp\left(-\frac{h_1\sqrt{\lambda D_1}}{D_1}\right)\right]}$ (18)

$$\left\{2C_{h_1+h_2}\sqrt{\lambda D_2} - C_{h_1}\sqrt{\lambda D_2}\left[\exp\left(\frac{h_2\sqrt{\lambda D_2}}{D_2}\right) + \exp\left(-\frac{h_2\sqrt{\lambda D_2}}{D_2}\right)\right]\right\}$$

$D_1 = 2.94 \times 10^{-9}$ m$^2$/s, $D_2 = 1.42 \times 10^{-8}$ m$^2$/s, $h_1 = 0.06$ m, $h_2 = 0.03$ m, $\lambda = 2.1 \times 10^{-6}$ s$^{-1}$ are substituted into the formula (18), to obtain $$k = \frac{1}{14\frac{C_{h_1+h_2}}{C_{h_1}} + 1}, \quad (19)$$

when $$\frac{C_{h_1+h_2}}{C_{h_1}}$$

is small enough, $k \approx 1$, that is, $J_1 \approx J_2$.

k is an intermediate parameter.

(4) Rapid Establishment of Radon Concentration in Radon Accumulation Chamber Upon Balance Radon in the radon accumulation chamber is all generated by the solid radon source, which takes excessively long time to reach a balance state. In order to rapidly establish the balance state of radon concentration in the radon accumulation chamber, a method for inflating radon into the radon accumulation chamber from gas flow solid radon source is adopted in the initial state. The change of radon concentration in the radon accumulation chamber is shown in formula (20):

$$\frac{dC}{dt} = \frac{\lambda \eta A_0}{V} - \frac{J_1 S}{V} - \lambda C. \quad (20)$$

When the radon concentration in the chamber reaches the balance state, let the left side of the formula (20) be 0, the radon concentration in the radon accumulation chamber is obtained, that is, the concentration of radon inflated into the radon accumulation chamber in the initial state is $C_e$.

$$C_e = \frac{1}{V}\left(\eta A_0 - \frac{J_1 S}{\lambda}\right), \quad (21)$$

because $J_1 \approx J_2$, the formula (14) is optimized into $$C_e = \frac{1}{V}\left(\eta A_0 - \frac{J_2 S}{\lambda}\right), \quad (22)$$

the formula (22) is transformed into $$A_0 = \frac{1}{\eta}\left(C_e V + \frac{J_2 S}{\lambda}\right). \quad (23)$$

According to the formula (23), a third unknown quantity can be calculated when any two parameters of the activity of the contained solid radon source, the concentration of the radon rapidly inflated into the radon accumulation chamber and the radon exhalation rate of the device surface are known, and the function relationships between any two parameters of the three parameters can be obtained by fitting.

(5) Radon Exhalation Rate Measured by an Activated Carbon-γ Spectrum Method

The activated carbon box is arranged upside down on the surface of the exhalation medium, and is circumferentially sealed with rubber mud. The time when radon accumulation process begins is recorded, and the accumulation time is set to be $t_1$. After the accumulation is completed, the activated carbon box is removed, and sealed for a waiting time of $t_2$. The activated carbon box is measured with a high-purity germanium spectrometer. After the measurement is completed, a net count N and a background counting rate B are recorded and substituted into the following formula for calculation:

$$J = \frac{(N-B)e^{\lambda t_2} \cdot \lambda}{Sk(1-e^{-\lambda t_1}) \times 3600}, \quad (24)$$

J: a radon exhalation rate, Bq/(m$^2$·s)

N: a net counting rate of γ characteristic peak 609 keV, cps;

B: a background counting rate, cps;

$t_1$: an accumulation time (h);

$t_2$: a time interval from the end of accumulation to the start of measurement, that is, waiting time (h);

λ: a decay constant of radon, 7.55×10$^{-3}$ h$^{-1}$;

S: a cross-sectional area of the activated carbon box, 0.006359 m$^2$;

K: a conversion factor, 0.007 cps/Bq.

In the present disclosure, the radon exhalation rate on the surface of the reference device is measured by the activated carbon adsorption method. The activated carbon adsorption method utilizes the adsorption of the exhaled radon by the activated carbon, obtains the radon exhalation rate by measuring the γ spectrum generated by the decay of the radon adsorbed in the activated carbon, and can validate the stability and uniformity of the measurement by the calibration device for the radon exhalation rate measuring instrument simultaneously.

Embodiment 3

The present disclosure discloses a method for measuring radon exhalation rate by a calibration device for a radon exhalation rate measuring instrument, including the following steps 101-104.

In step 101, the activated carbon box is arranged upside down on the diffusion medium, and a sealing treatment is performed between the activated carbon box and the diffusion medium.

In step 102, after a first set time elapses, the activated carbon box is removed and sealed.

In step 103, after a second set time elapses, the activated carbon box is measured with a high-purity germanium spectrometer to obtain the net count rate and background count rate of γ characteristic peak 609 keV.

In step 104, a radon exhalation rate is determined according to the first set time, the second set time, the net count rate, and the background count rate.

Step 104 specifically includes calculating the radon exhalation rate according to the formula (24).

Figure 10:
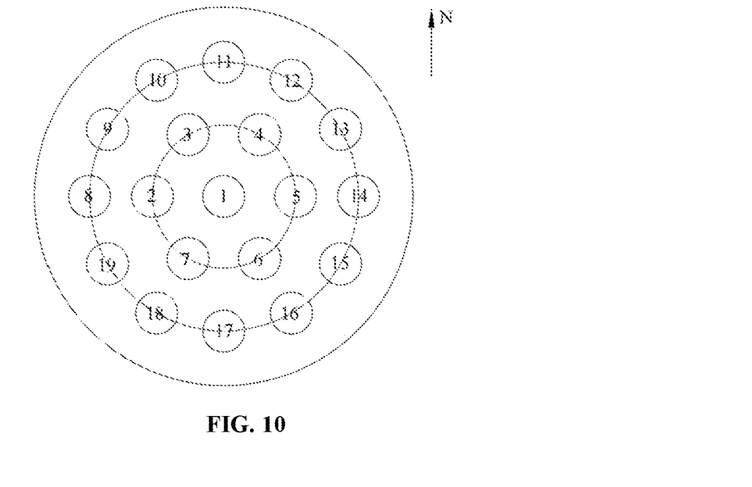
FIG. 10 is a diagram showing placement points of activated carbon boxes according to the present disclosure.

The present disclosure adopts the activated carbon adsorption method to measure the radon exhalation rate of the calibration device for the radon exhalation rate measuring instrument. The placement points of the activated carbon box on the diffusion medium are shown in FIG. 10, and measurement results of the radon exhalation rate are shown in Table 2.

theoretical value is in good agreement with the measured value, which proves the excellent performance of the experiment and calibration device for radon exhalation rate measuring instrument.

Embodiment 4

The present disclosure discloses a radon exhalation rate control method applied to a calibration device for a radon exhalation rate measuring instrument disclosed in Embodiment 1, the radon exhalation rate control method including the following step.

The radon exhalation rate of the calibration device for the radon exhalation rate measuring instrument is adjusted by changing the activity of a solid radon source in the radon accumulation chamber and the thickness of the diffusion medium layer of the calibration device for the radon exhalation rate measuring instrument, and different verified radon exhalation rate measuring instruments are calibrated by adjusting the radon exhalation rate of the calibration device for the radon exhalation rate measuring instrument.

An adjustment process for radon exhalation rate specifically includes the following steps 1-5.

In step 1, thicknesses of the plasterboard and the high-density wood board in the diffusion medium are determined.

In step 2, a relationship among diffusive solid radon sources with different activities and the radon exhalation rates and radon concentrations in the radon accumulation chamber is determined.

The relationship among diffusive solid radon sources with different activities and the radon exhalation rates and the radon concentrations in the radon accumulation chamber includes the relationship between the radon exhalation rate

TABLE 2

Stability and uniformity measurement of 100000 Bq diffusion source

| Placement points of activated carbon boxes | Radon exhalation rate/mBq/(m² · s) | | | | Relative uncertainty $u_r$ |
|---|---|---|---|---|---|
| | First measurement | Second measurement | Third measurement | Mean ± SD | |
| 1 | 187.09 | 190.26 | 190.26 | 189.20 ± 1.83 | 0.97% |
| 2 | 195.75 | 190.98 | 195.75 | 194.16 ± 2.75 | 1.42% |
| 3 | 194.89 | 191.7 | 193.3 | 193.30 ± 1.60 | 0.83% |
| 4 | 187.61 | 184.41 | 189.22 | 187.08 ± 2.45 | 1.31% |
| 5 | 189.93 | 186.71 | 189.93 | 188.86 ± 1.86 | 0.98% |
| 6 | 192.27 | 189.04 | 198.73 | 193.35 ± 4.93 | 2.55% |
| 7 | 196.24 | 193 | 197.86 | 195.70 ± 2.47 | 1.26% |
| 8 | 200.24 | 192.1 | 200.24 | 197.53 ± 4.70 | 2.38% |
| 9 | 202.63 | 199.36 | 201 | 201.00 ± 1.64 | 0.81% |
| 10 | 203.4 | 201.76 | 198.48 | 201.21 ± 2.51 | 1.25% |
| 11 | 204.17 | 200.87 | 199.23 | 201.42 ± 2.52 | 1.25% |
| 12 | 201.63 | 196.67 | 196.67 | 198.32 ± 2.86 | 1.44% |
| 13 | 199.08 | 197.42 | 197.42 | 197.97 ± 0.96 | 0.48% |
| 14 | 198.17 | 198.17 | 203.16 | 199.83 ± 2.88 | 1.44% |
| 15 | 205.6 | 200.59 | 203.93 | 203.37 ± 2.55 | 1.25% |
| 16 | 204.7 | 201.35 | 204.7 | 203.58 ± 1.93 | 0.95% |
| 17 | 202.11 | 203.79 | 205.48 | 203.79 ± 1.69 | 0.83% |
| 18 | 202.87 | 204.56 | 204.56 | 204.00 ± 0.98 | 0.48% |
| 19 | 203.64 | 203.64 | 205.34 | 204.21 ± 0.98 | 0.48% |
| Mean ± SD | 198.53 ± 5.87 | 196.13 ± 6.18 | 198.70 ± 5.26 | 197.78 ± 2.32 | 1.18% |
| Relative uncertainty $u_r$ | 2.96% | 3.15% | 2.65% | | |

It can be seen from Table 2 that the stability of radon exhalation rate of the device is less than 5% and the uniformity thereof is less than 5% when the device selects a diffusive solid radon source with activity of 100000 Bq. The and the activity of diffusive solid radon source, and the relationship among the activity of diffusive solid radon source, the radon exhalation rate and the radon concentration in the radon accumulation chamber.

With the calibration device for the radon exhalation rate measuring instrument, different levels of uniform and stable radon exhalation rates can be formed on the surface of the exhalation medium by changing the activity of the solid radon source, and put into the calibration device, respectively. The radon exhalation can reach a stable state quickly by inflating the radon accumulation chamber with a radon source. The relationship between the radon exhalation rate and the activity of the diffusive solid radon source can be obtained by measuring the radon exhalation rate at the middle point of the exhalation medium with the activated carbon-γ spectrum method, and the results are shown in FIG. 11.

Figure 11:
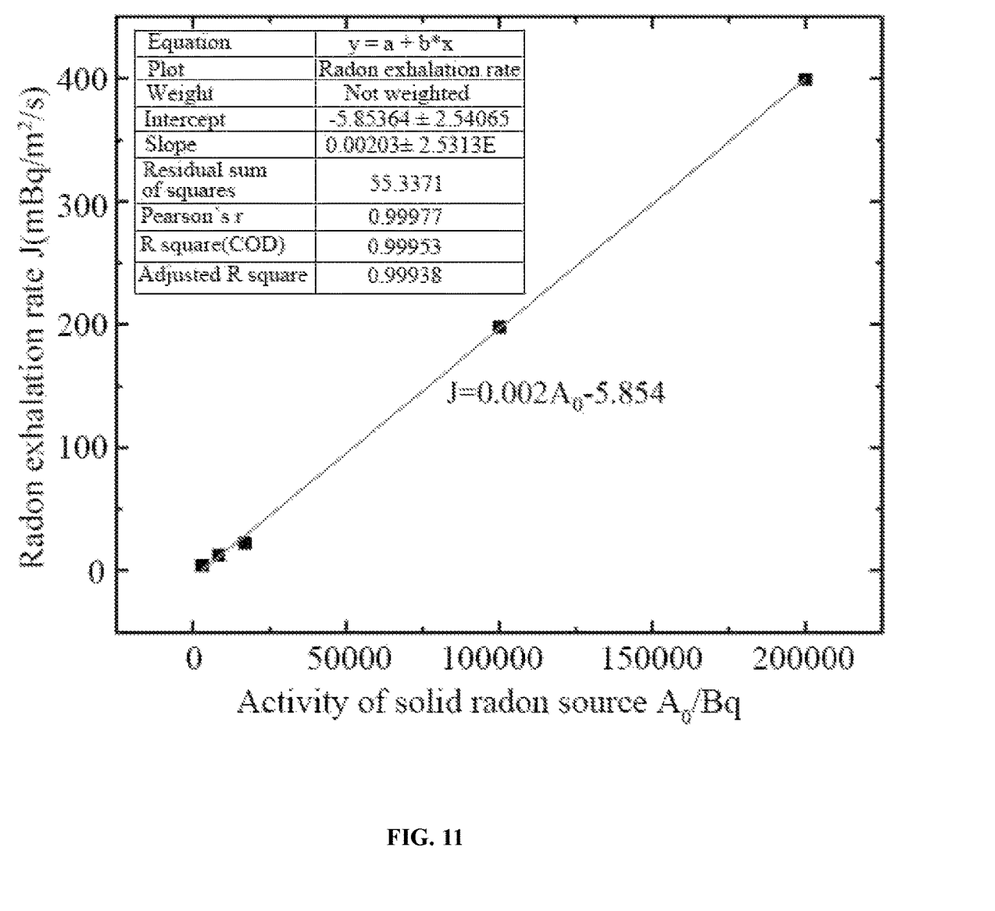
FIG. 11 shows a relationship between the radon exhalation rate and an activity of the solid radon source according to the present disclosure.

As can be seen from FIG. 11, a linear fitting equation between the radon exhalation rate J in the calibration device and the activity $A_0$ of the placed diffusive solid radon source is obtained by linear fitting of the data, $$J = 0.002A_0 - 5.854$$

$R^2$ indicates a discrete degree of data, which is a measure of the fitting degree of the regression equation as a whole, and is a representation of the overall relationship between dependent variables and all independent variables. $R^2$ equals to the ratio of the regression sum of squares to the total sum of squares, i.e., the percentage of variability of the dependent variable that can be explained by the regression equation. The closer the value of $R^2$ to 1, the better the equation fitting effect. When $R^2=0.99$ in the fitting equation is close to 1, linear fitting is reasonable. When the activity of the radon source placed in the calibration device is known, the value of the radon exhalation rate of the reference device can be quickly obtained by the fitting equation. In the later stage, the calibration device for the radon exhalation rate measuring instrument provides the required reference value of solid radon activity for obtaining a higher radon exhalation rate, which greatly improves the experimental efficiency.

According to the formula (23), when the activity of the placed diffusive solid radon source and the radon exhalation rate are known, the radon concentration of the radon accumulation chamber can be calculated.

In step 3, based on the relationship among diffusive solid radon sources with different activities and the radon exhalation rates and the radon concentrations in the radon accumulation chamber, a diffusive solid radon source is selected according to the radon exhalation rate to be adjusted.

In step 4, a stable radon concentration of the radon accumulation chamber is determined according to a selected diffusive solid radon source.

In step 5, the selected diffusive solid radon source is placed in the solid radon source containing chamber, the radon accumulation chamber is inflated with a predetermined amount of radon from the gas flow solid radon source, and wait for the radon concentration in the radon accumulation chamber to reach the equilibrium state.

When the radon exhalation rate to be adjusted changes, if the thicknesses of the plasterboard and the high-density wood board in the diffusion medium do not change, steps 3-5 are repeated to adjust the radon exhalation rate.

When the radon exhalation rate to be adjusted changes, if the thicknesses of the plasterboard and the high-density wood board in the diffusion medium change, steps 1-5 are repeated to adjust the radon exhalation rate.

Embodiments of the present specification are described in a progressive manner, each embodiment focuses on the difference from other embodiments, and the same and similar parts between the embodiments may refer to each other. Since the device disclosed in an embodiment corresponds to the method disclosed in another embodiment, the description is relatively simple, and reference can be made to the method description.

In this specification, some specific embodiments are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and the scope of application in accordance with the ideas of the present disclosure. In conclusion, the content of this specification shall not be construed as limitations to the present disclosure.

What is claimed is:

1. A calibration device for a radon exhalation rate measuring instrument, comprising a diffusive solid radon source, a solid radon source containing chamber, a radon accumulation chamber, a diffusion medium and an air pressure balancing device, wherein the radon accumulation chamber is shaped as an inverted cone, a circular cone opening at a bottom of the radon accumulation chamber is connected with the solid radon source containing chamber, a top of the radon accumulation chamber is connected with the diffusion medium, the diffusion medium comprises a plasterboard and a high-density wood board, the plasterboard is located above the radon accumulation chamber, the high-density wood board is overlapped on the plasterboard, the air pressure balancing device is connected with the radon accumulation chamber, and configured to maintain air pressure dynamic balance between the radon accumulation chamber and ambient atmosphere;

a radon exhalation rate of a surface of the diffusion medium is determined according to a diffusion coefficient of radon in the diffusion medium, a thickness of a diffusion medium layer, and an activity of a solid radon source in the solid radon source containing chamber;

the radon exhalation rate is adjusted by changing the activity of the solid radon source in the solid radon source containing chamber and the thickness of the diffusion medium layer.

2. The calibration device according to claim 1, further comprising a support frame and a fixture for fixing the diffusion medium layer, wherein the fixture comprises an upper fastening flange, a lower fastening flange, a fastening screw and a holding plate, the holding plate is arranged at an edge of the diffusion medium layer for holding, the fastening screw is configured to have an adjustable length and pass through the holding plate, and the upper fastening flange and the lower fastening flange are respectively located at two ends of the fastening screw for fastening the holding plate;

the support frame is connected with a bottom of the fixture, the support frame is configured to support the radon accumulation chamber, and both the support frame and the radon accumulation chamber are made of stainless steel material;

a universal wheel is arranged at a bottom of the support frame.

3. The calibration device according to claim 2, further comprising a housing, wherein the housing is cylindrical, the housing is sleeved on outer sides of the support frame and the diffusion medium, and the housing is made of stainless steel material.

4. The calibration device according to claim 2, wherein the radon accumulation chamber is connected with the solid radon source containing chamber in a flange connection manner, and has a silicone gasket provided therebetween.

5. The calibration device according to claim 1, wherein a silicone gasket is arranged between the high-density wood board and the plasterboard.

6. The calibration device according to claim 1, wherein the air pressure balancing device comprises a U-shaped connecting pipe and an air pressure balancing bottle, the air pressure balancing bottle is connected with the radon accumulation chamber through the U-shaped connecting pipe, and liquid in the air pressure balancing bottle is a saline mixture with a salt concentration exceeding a predetermined salt concentration.

7. The calibration device according to claim 1, wherein a side wall of the radon accumulation chamber is provided with a first inlet and a second inlet, which are symmetrically distributed on the side wall of the radon accumulation chamber, and through which a predetermined amount of radon is rapidly inflated from a gas flow solid radon source into the radon accumulation chamber.

8. The calibration device according to claim 1, wherein a cross support is arranged at a top opening of the radon accumulation chamber.

9. A radon exhalation rate control method, which is applied to a calibration device for a radon exhalation rate measuring instrument, comprising a diffusive solid radon source, a solid radon source containing chamber, a radon accumulation chamber, a diffusion medium and an air pressure balancing device, wherein the radon accumulation chamber is shaped as an inverted cone, a circular cone opening at a bottom of the radon accumulation chamber is connected with the solid radon source containing chamber, a top of the radon accumulation chamber is connected with the diffusion medium, the diffusion medium comprises a plasterboard and a high-density wood board, the plasterboard is located above the radon accumulation chamber, the high-density wood board is overlapped on the plasterboard, the air pressure balancing device is connected with the radon accumulation chamber, and configured to maintain air pressure dynamic balance between the radon accumulation chamber and ambient atmosphere;

a radon exhalation rate of a surface of the diffusion medium is determined according to a diffusion coefficient of radon in the diffusion medium, a thickness of a diffusion medium layer, and an activity of a solid radon source in the solid radon source containing chamber;

the radon exhalation rate is adjusted by changing the activity of the solid radon source in the solid radon source containing chamber and the thickness of the diffusion medium layer, the radon exhalation rate control method comprising:

adjusting the radon exhalation rate of the calibration device by changing the activity of the solid radon source in the radon accumulation chamber and the thickness of the diffusion medium layer of the calibration device, and calibrating different verified radon exhalation rate measuring instruments by adjusting the radon exhalation rate of the calibration device;

an adjustment process for a radon exhalation rate to be adjusted comprises:

step 1: determining thicknesses of the plasterboard and the high-density wood board in the diffusion medium;

step 2: determining a relationship among diffusive solid radon sources with different activities and radon exhalation rates and radon concentrations in the radon accumulation chamber;

step 3: based on the relationship among the diffusive solid radon sources with different activities and the radon exhalation rates and the radon concentrations in the radon accumulation chamber, selecting a diffusive solid radon source according to the radon exhalation rate to be adjusted;

step 4: determining a stable radon concentration in the radon accumulation chamber according to a selected diffusive solid radon source;

step 5: placing the selected diffusive solid radon source in the solid radon source containing chamber, inflating the radon accumulation chamber with a predetermined amount of radon from a gas flow solid radon source, and waiting for the radon concentration in the radon accumulation chamber to reach a balance state;

when the radon exhalation rate to be adjusted changes, if the thicknesses of the plasterboard and the high-density wood board in the diffusion medium do not change, repeating steps 3-5 to adjust the radon exhalation rate;

when the radon exhalation rate to be adjusted changes, if the thicknesses of the plasterboard and the high-density wood board in the diffusion medium change, repeating steps 1-5 to adjust the radon exhalation rate.

10. The radon exhalation rate control method according to claim 9, wherein the calibration device further comprises a support frame and a fixture for fixing the diffusion medium layer, wherein the fixture comprises an upper fastening flange, a lower fastening flange, a fastening screw and a holding plate, the holding plate is arranged at an edge of the diffusion medium layer for holding, the fastening screw is configured to have an adjustable length and pass through the holding plate, and the upper fastening flange and the lower fastening flange are respectively located at two ends of the fastening screw for fastening the holding plate;

the support frame is connected with a bottom of the fixture, the support frame is configured to support the radon accumulation chamber, and both the support frame and the radon accumulation chamber are made of stainless steel material;

a universal wheel is arranged at a bottom of the support frame.

11. The radon exhalation rate control method according to claim 10, wherein the calibration device further comprises a housing, wherein the housing is cylindrical, the housing is sleeved on outer sides of the support frame and the diffusion medium, and the housing is made of stainless steel material.

12. The radon exhalation rate control method according to claim 10, wherein the radon accumulation chamber is connected with the solid radon source containing chamber in a flange connection manner, and has a silicone gasket provided therebetween.

13. The radon exhalation rate control method according to claim 9, wherein a silicone gasket is arranged between the high-density wood board and the plasterboard.

14. The radon exhalation rate control method according to claim 9, wherein the air pressure balancing device comprises a U-shaped connecting pipe and an air pressure balancing bottle, the air pressure balancing bottle is connected with the radon accumulation chamber through the U-shaped connecting pipe, and liquid in the air pressure balancing bottle is a saline mixture with a salt concentration exceeding a predetermined salt concentration.

15. The radon exhalation rate control method according to claim 9, wherein a side wall of the radon accumulation chamber is provided with a first inlet and a second inlet, which are symmetrically distributed on the side wall of the radon accumulation chamber, and through which a predetermined amount of radon is rapidly inflated from a gas flow solid radon source into the radon accumulation chamber.

16. The radon exhalation rate control method according to claim 9, wherein a cross support is arranged at a top opening of the radon accumulation chamber.

\* \* \* \* \*